(12) United States Patent
Harvey et al.

(10) Patent No.: US 8,993,689 B1
(45) Date of Patent: *Mar. 31, 2015

(54) POLYPHENOLS AND HIGH-PERFORMANCE RESINS FROM SYRINGALDEHYDE

(71) Applicant: United States of America as Represented by the Secretary of the Navy, Washington, DC (US)

(72) Inventors: Benjamin G. Harvey, Ridgecrest, CA (US); Matthew C. Davis, Ridgecrest, CA (US); Heather A. Meylemans, Ridgecrest, CA (US); William Lai, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,701

(22) Filed: Feb. 4, 2014

Related U.S. Application Data

(63) Continuation of application No. 14/172,673, filed on Feb. 4, 2014.

(60) Provisional application No. 61/769,297, filed on Feb. 26, 2013.

(51) Int. Cl.
| | | |
|---|---|---|
| *C07C 37/055* | (2006.01) | |
| *C07C 37/20* | (2006.01) | |
| *C08G 18/00* | (2006.01) | |
| *C08L 79/00* | (2006.01) | |

(52) U.S. Cl.
CPC ............... *C08G 18/00* (2013.01); *C08L 79/00* (2013.01)
USPC ........................................................ 525/452

(58) Field of Classification Search
CPC .................................................. C07C 37/055
USPC .......... 568/309, 646, 807, 811, 813; 564/102, 564/251; 524/589; 525/452, 523; 562/470; 523/400; 435/320.1, 252.3, 189, 165
See application file for complete search history.

(56) References Cited

U.S. PATENT DOCUMENTS 4,087,336 A 5/1978 Wagenknecht

FOREIGN PATENT DOCUMENTS

CN 1736986 A 2/2006

OTHER PUBLICATIONS

Dieguez, H. R. et al. J. Am. Chem. Soc. 2010, 132, 254-259 describes the synthesis of 3,3'-5,5'tetramethoxystilbene via Cp2TiCl mediated reductive coupling.

*Primary Examiner* — Randy Gulakowski
*Assistant Examiner* — Christopher M Rodd
(74) *Attorney, Agent, or Firm* — Charlene A. Haley

(57) ABSTRACT

A method to generate renewable high performance composites and thermoplastics. These materials can be generated from a renewable phenol (syringaldehyde) that can be derived from lignocellulosic biomass. The use of syringaldehyde as a precursor to composites has the potential to reduce the cost and environmental impact of structural materials, while meeting or exceeding the performance of current petroleum derived resins.

18 Claims, 1 Drawing Sheet

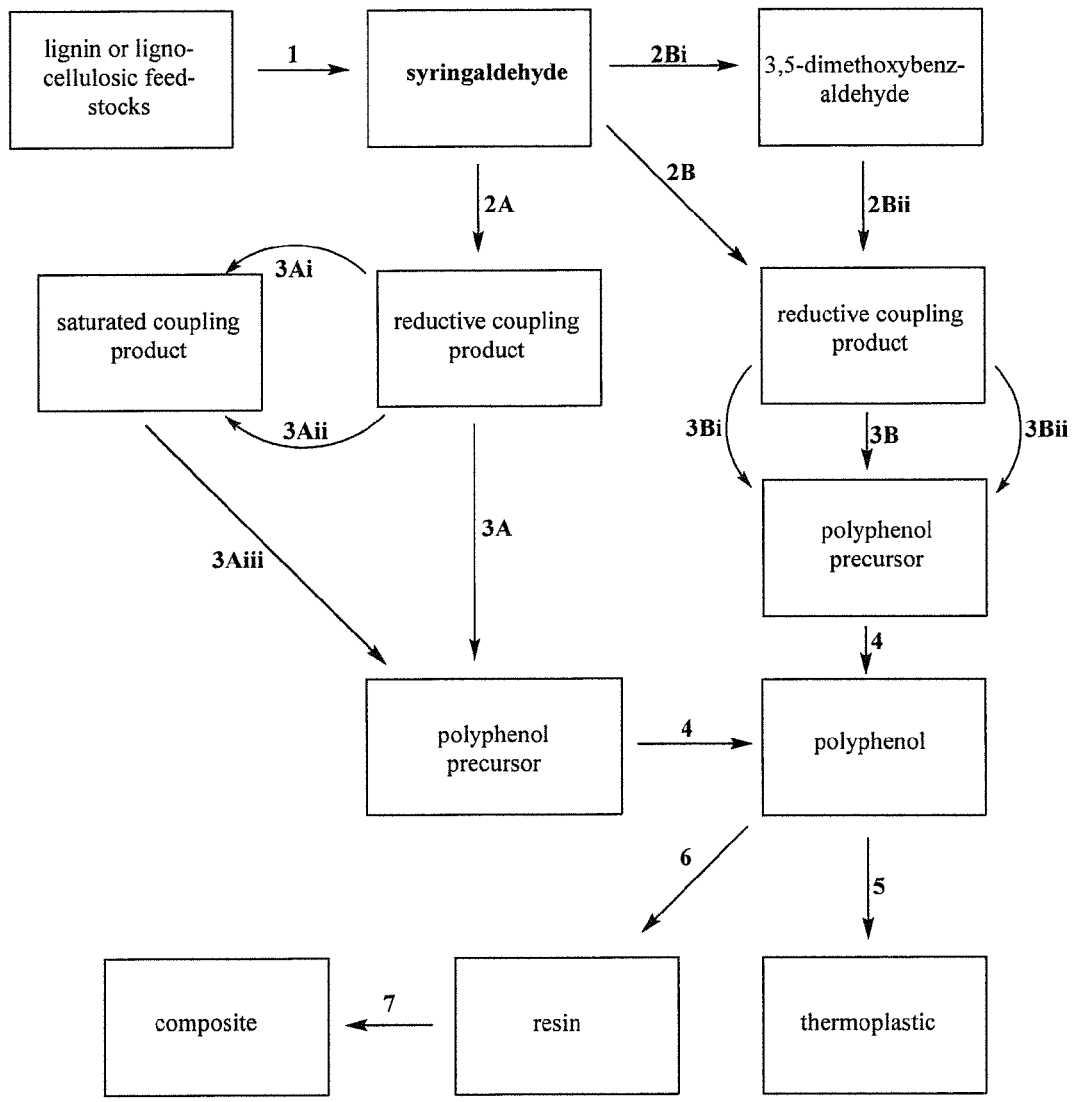

POLYPHENOLS AND HIGH-PERFORMANCE RESINS FROM SYRINGALDEHYDE

CROSS-REFERENCE TO RELATED APPLICATIONS

This is a non-provisional patent application, claiming the benefit of, parent application Ser. No. 61/769,297 filed on Feb. 26, 2013, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods to efficiently generate polyphenols, thermoplastics, and high temperature resins/thermosets from syringaldehyde. High value phenolic compounds including trans-resveratrol can be generated by this approach.

BRIEF DESCRIPTION OF THE DRAWING

FIG. 1 is a flow chart showing methods to efficiently generate polyphenols, thermoplastics, and high temperature resins/thermosets from syringaldehyde, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to methods to generate renewable high performance composites and thermoplastics. These materials can be generated from a renewable phenol (syringaldehyde) that can be derived from lignocellulosic biomass. The use of syringaldehyde as a precursor to composites has the potential to reduce the cost and environmental impact of structural materials, while meeting or exceeding the performance of current petroleum derived resins.

Bisphenol compounds such as BPA (bisphenol A) are widely used as building blocks for a variety of commercial and industrial products. Specifically, bisphenols are the building blocks for polycarbonate plastics, epoxy resins, polyester resins, cyanate ester resins and other polymers/resins which include but are not limited to polycarbonates, polysulfones, polyesters, polyester-styrene, alkylphenolics, and polyalylates. Commercially available bisphenol compounds, especially polyaromatic bisphenols, are currently derived from petroleum.

In an effort to create more sustainable bisphenol building blocks we have developed a series of polyaromatic bisphenol compounds derived from syringaldehyde. Syringaldehyde can be isolated from crude biomass feedstocks that include lignin and the current invention describes a method to efficiently convert syringaldehyde into polyphenols. The ability to either homocouple syringaldehyde or cross-couple syringaldehyde with various renewable aldehydes allows for the synthesis of a variety of trifunctional and tetrafunctional bisphenols that can be converted to resins with exceptional glass transition temperatures. The utilization of renewable polyphenols as precursors to epoxies, polycarbonates, and high temperature thermosets including cyanate esters, provides an opportunity to develop full-performance resins while reducing the use of petroleum based feedstocks. This approach will then diminish the overall environmental impact of resin production while allowing for a sustainable source of phenols.

Some references in the literature include: CN 1736986 A describes the synthesis of 3,3'-5,5'-tetramethoxystilbene via a Wittig reaction; U.S. Pat. No. 4,087,336 describes electrochemical reduction of various p-benzaldehydes to stilbenes; and Dieguez, H. R. et al. J. Am. Chem. Soc. 2010, 132, 254-259 describes the synthesis of 3,3'-5,5'tetramethoxystilbene via $Cp_2TiCl$ mediated reductive coupling.

FIG. 1. is a flow chart showing methods to efficiently generate polyphenols, thermoplastics, and high temperature resins/thermosets from syringaldehyde.

1. Syringaldehyde is isolated from a renewable source (lignin). This step can include oxidation of lignin with oxygen, peroxides, or aromatic nitro-compounds among others. The oxidation step can be conducted with or without a transition metal catalyst. Syringaldehyde can also be recovered from the black liquor resulting from the Kraft pulping process.

2A. Syringaldehyde is directly coupled to a renewable aldehyde through chemical or electrochemical means. This step can be conducted via a transition metal mediated McMurry coupling or by applying a potential in a standard electrochemical setup to reductively couple the aldehydes.

3A. The reductively coupled product is converted to a polyphenol precursor by the following steps:

3Ai. Reductive coupling products generated by a McMurry reaction are hydrogenated to generate a saturated coupling product.

3Aii. The vicinal diols of reductive coupling products generated electrochemically are either reduced by hydrogenation or are protected and then reductively eliminated 3Aiii. Saturated coupling products are then converted to polyphenol precursors by dehydrodeoxygenation which is accomplished via conversion of phenols to sulfonates and subsequent reductive elimination with transition metal catalysts.

Alternate method for generation of polyphenol precursors:

2B. Syringaldehyde is converted to a reductive coupling product by:

2Bi. conversion to a sulfonate followed by reductive elimination to yield 3,5-dimethoxybenzaldehyde.

2Bii. 3,5-dimethoxybenzaldehyde is reductively coupled either by a transition metal mediated McMurry reaction or electrochemically to yield a reductive coupling product.

3B. Reductive coupling products are converted to polyphenol precursors by the following steps:

3Bi. Reductive coupling products generated by a McMurry reaction are hydrogenated to directly yield a polyphenol precursor 3Bii. The vicinal diols of electrochemically generated reductive coupling products are either reduced by hydrogenation or are protected and then undergo reductive elimination to generate a polyphenol precursor.

4. Polyphenol precursors are converted to polyphenols by a demethylation reaction. Reagents for this step may include $BBr_3$ or pyridinium hydrochloride.

5. Polyphenols are converted to thermoplastics by methods known in the art.

6. Alternatively, polyphenols can be converted to resins including cyanate ester and epoxy resins.

7. Resins can be blended with support materials including glass or carbon fibers and thermally cured with or without a catalyst to generate a composite material.

The McMurry reaction is an organic chemical reaction under which two ketone or aldehyde groups combine to form an alkene in the presence of a titanium species resulting from reduction of a titanium (III or IV) compound with a reducing metal such as magnesium or zinc. The reaction may occur by a free radical process, similar to that observed in the pinacol coupling of aldehydes and ketones in the presence of a reducing metal, followed by an elimination of oxo-titanium species, owing to the strong bond that oxygen and titanium share. In some cases McMurry reactions can be catalytic with respect to titanium when stoichiometric chlorinating agents such as alkyl silyl chlorides are added to the reaction mixture. Other transition metal compounds based on tungsten are also effective at mediating McMurry reactions.

The electrochemical coupling can be achieved by applying the appropriate voltage to a salt solution including the two ketones or aldehydes including compounds to form a coupled diol product. The reaction is run using a standard three electrode setup where the working and auxiliary electrodes are selected from lead, platinum, mercury, nickel, gold, or carbon; and performed at any voltage at which hydrogen evolution occurs at the chosen electrode. After the reaction the product diol is precipitated from the salt solution by acidification.

Syringaldehyde can be isolated from lignin or lignocellulosic feedstocks by chemical or enzymatic oxidation. It can also be prepared from other lignin decomposition products including vanillin. There are several methods available to couple syringaldehyde to other aldehydes. A direct chemical method including McMurry coupling can be utilized to combine the two aldehydes with generation of a double bond. Alternatively, an electrochemical method can be utilized to generate a diol. The diol can then be chemically reduced by various methods including hydrogenation or protection/deprotection through either chemical or electrochemical methods. In embodiments, the diol can be converted to a diacetate or oxalate and then reduced to the olefin electrochemically. When a mixture of aldehydes is utilized, a distribution of homocoupling and cross-coupling products will result. In some cases, the distribution can be controlled by the reactivity of a given aldehyde. The distribution can also in some cases be controlled by solubility. Mixtures of coupled products can be used directly or purified through various means including crystallization, column chromatography, distillation, and sublimation. Dehydrodeoxygenation can be accomplished by conversion of the phenol to a sulfonate (e.g. mesylate, tosylate, triflate). Reaction with zero valent nickel or palladium then results in reductive elimination. Both heterogeneous and homogenous catalysts are suitable for the reductive elimination. The methoxy groups can be converted to hydroxy groups by a variety of methods including reaction with boron tribromide ($BBr_3$) or pyridinium hydrochloride. Dehydrodeoxygenation is conducted as in steps described above. The resulting aldehyde is coupled as described above. In the case of electrochemical coupling of molecules with limited solubility in water, a non-aqueous solvent with a broad electrochemical window, including acetonitrile, is used and an additional hydrogen source must be introduced. Various resins can be prepared from the polyphenols by techniques known in the art. In embodiments, the polyphenols can be converted to cyanate esters by reaction with a suitable base and a cyanogen halide. Polyphenols can also be converted to epoxy resins by reaction with epichlorohydrin. Various thermoplastics can be prepared from the polyphenols by techniques known in the art. In embodiments, the polyphenols can be converted to polycarbonates by reaction with reagents including phosgene, triphosgene, and diphenylcarbonate. In other embodiments, thermoplastics including polysulfones, polyesters, polyester-styrene polymers, alkylphenolics, and polyalylates can be prepared from the polyphenols. Composites can be fabricated by combining resins or thermoplastics with various fibers (including carbon or glass fibers) and curing the composites through either thermal or chemical means.

In other embodiments, please see the schematics and reaction schemes herein. Scheme 1 illustrates the process by which syringaldehyde is first deoxygenated to 3,5-dimethoxybenzaldehyde in two steps. The phenol is converted to a mesylate, tosylate, or triflate. Then reductive elimination is achieved by reaction with zero valent nickel or palladium to produce the benzaldehyde. The 3,5-dimethoxybenzaldehyde is then used in the McMurry coupling reaction either alone or with another aldehyde or ketone to produce either the homo-coupled or hetero-coupled product, respectively. The coupled product is then hydrogenated under standard conditions with Pt, Pd, or Ni under ~40 psi of hydrogen. The saturated product is then demethylated using a catalyst including pyridinium hydrochloride or boron tribromide to give the polyphenol. The polyphenol is then reacted with cyanogen bromide or a similar cyanogen halide or pseudohalide and a base including triethylamine to yield the cyanate ester.

Scheme 2 illustrates the process by which syringaldehyde is first deoxygenated to 3,5-dimethoxybenzaldehyde in two steps. The phenol is converted to a mesylate, tosylate, or triflate. Then reductive elimination is achieved by reaction with zero valent nickel or palladium to produce the benzaldehyde. The 3,5-dimethoxybenzaldehyde is then used in an electrochemical coupling reaction either alone or with another aldehyde or ketone to produce either the homo-coupled or hetero-coupled diol product, respectively. The coupled product is then reduced either through hydrogenation, or protection and reductive elimination (chemically or electrochemically) to produce a polyphenol precursor. The polyphenol precursor is then demethylated using a catalyst including pyridinium hydrochloride or boron tribromide to give the polyphenol. The polyphenol is then reacted with cyanogen bromide or a similar cyanogen halide or pseudohalide and a base including triethylamine to yield the cyanate ester.

Scheme 3 illustrates the process by which syringaldehyde is first used in the McMurry coupling reaction either alone or with another aldehyde or ketone to produce either the homo-coupled or hetero-coupled product, respectively. The coupled product is then hydrogenated under standard conditions with Pt, Pd, or Ni under ~40 psi of hydrogen. The coupled products are then deoxygenated in two steps. Deoxygenation takes place by converting the phenol to a sulfonate (e.g. mesylate, tosylate, or triflate). Then reductive elimination is achieved by reaction with zero valent nickel or palladium to produce the polyphenol precursor. The deoxygenated product is then demethylated using a catalyst including pyridinium hydrochloride or boron tribromide to give the polyphenol. The polyphenol is then reacted with cyanogen bromide or a similar cyanogen halide or pseudohalide and a base including triethylamine to yield the cyanate ester.

Scheme 4 illustrates the process by which syringaldehyde is used in the electrochemical coupling reaction either alone or with another aldehyde or ketone to produce either the homo-coupled or hetero-coupled diol product, respectively. The coupled diol product is then reduced either through hydrogenation or protection and reductive elimination (chemically or electrochemically) to produce the saturated product. The coupled product is then deoxygenated in two steps. Deoxygenation takes place by converting the phenol to a sulfonate (e.g. mesylate, tosylate, or triflate). Then reductive elimination is achieved by reaction with zero valent nickel or palladium to produce the polyphenol precursor. The deoxygenated product is then demethylated using a catalyst including pyridinium hydrochloride or boron tribromide to give the polyphenol. The polyphenol is then reacted with cyanogen bromide or similar cyanogen halide and a base including triethylamine to yield the cyanate ester.

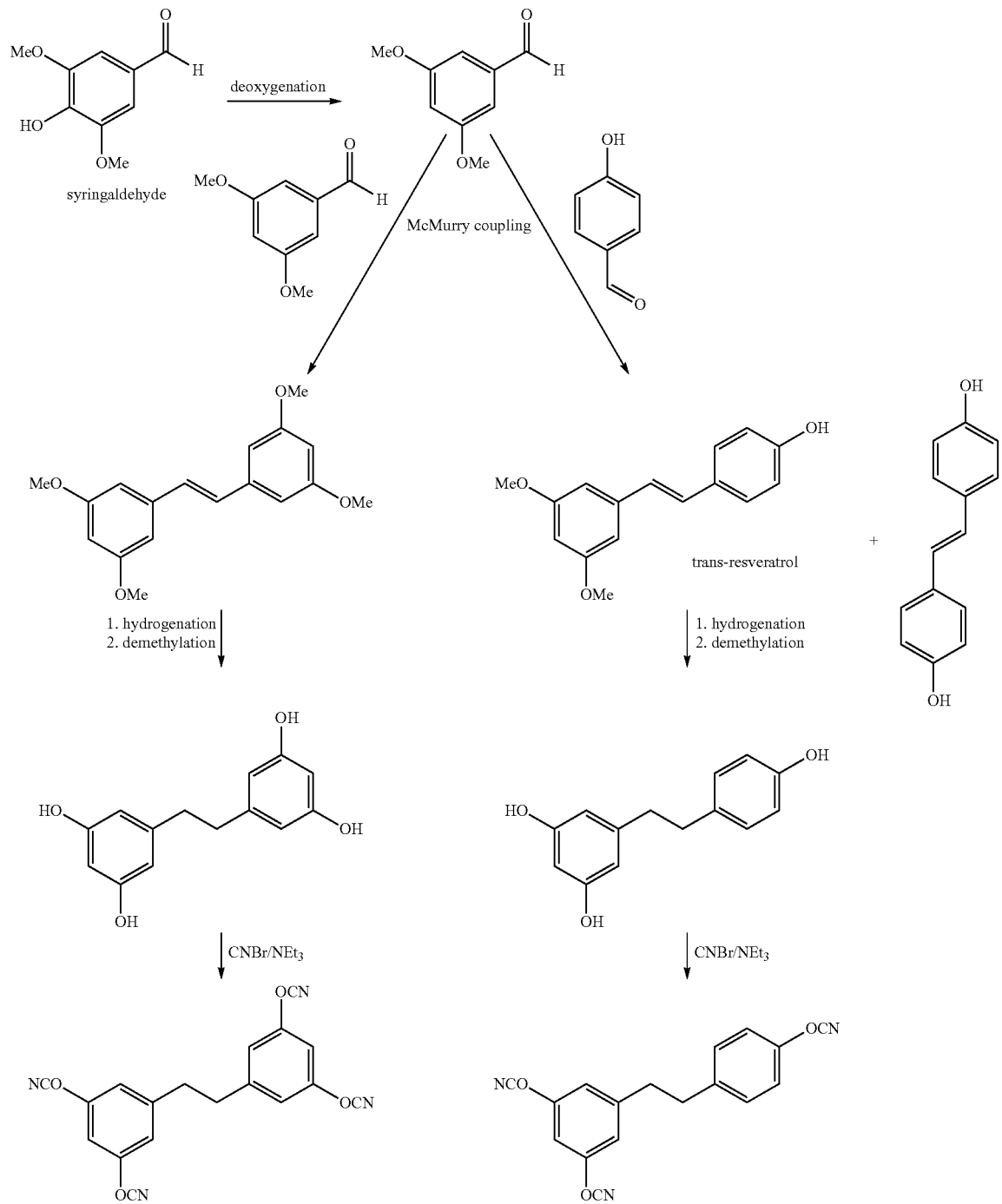

Scheme 1. Conversion of syringaldehyde to cyanate esters by initial dehydrodeoxygenation followed by a McMurry coupling.

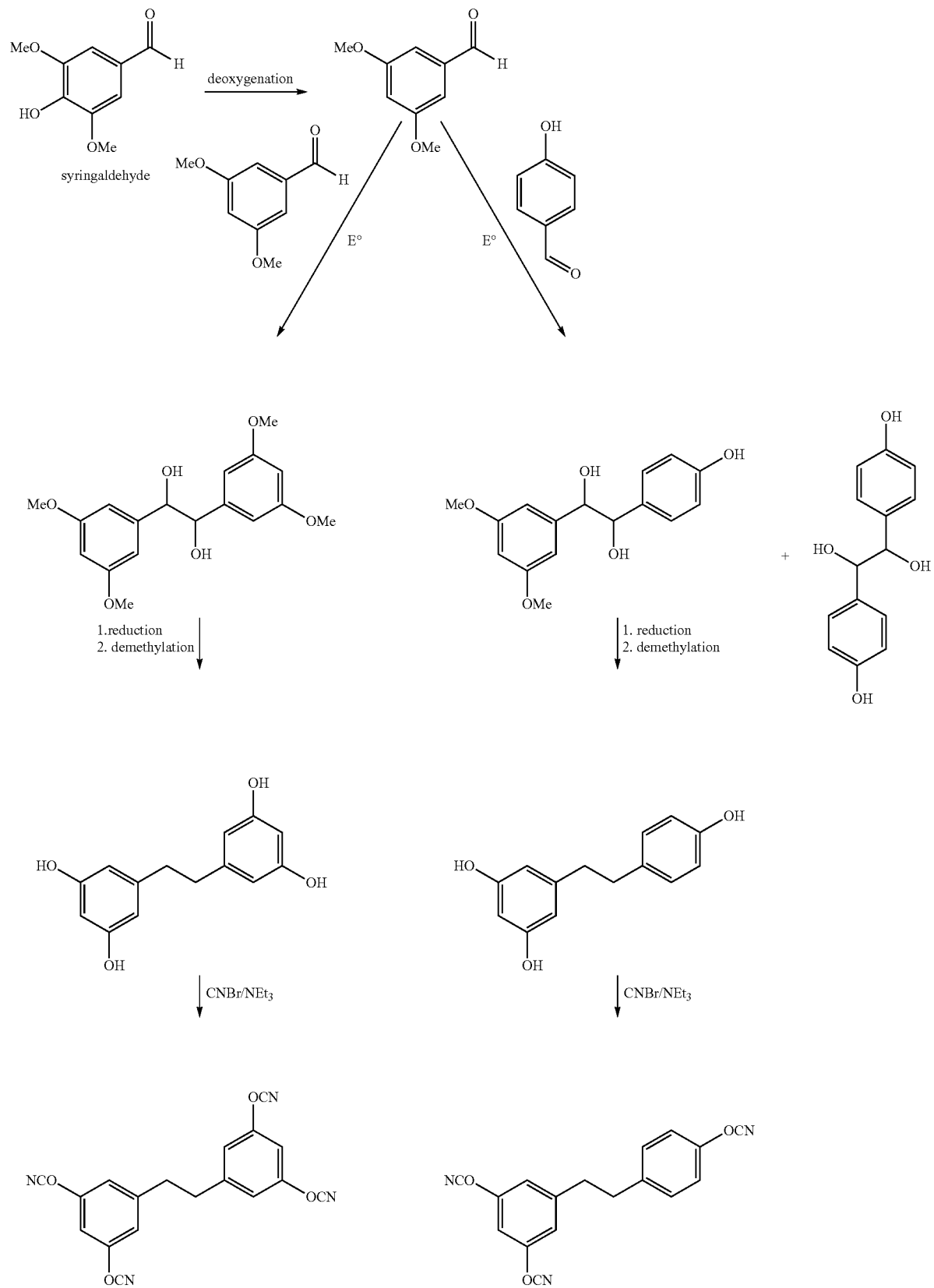
Scheme 2. Conversion of syringaldehyde to cyanate esters with initial dehydrodeoxygenation followed by a reductive electrochemical coupling.

Scheme 3. Conversion of syringaldehyde to cyanate esters without initial dehydrodeoxygenation (McMurry coupling)
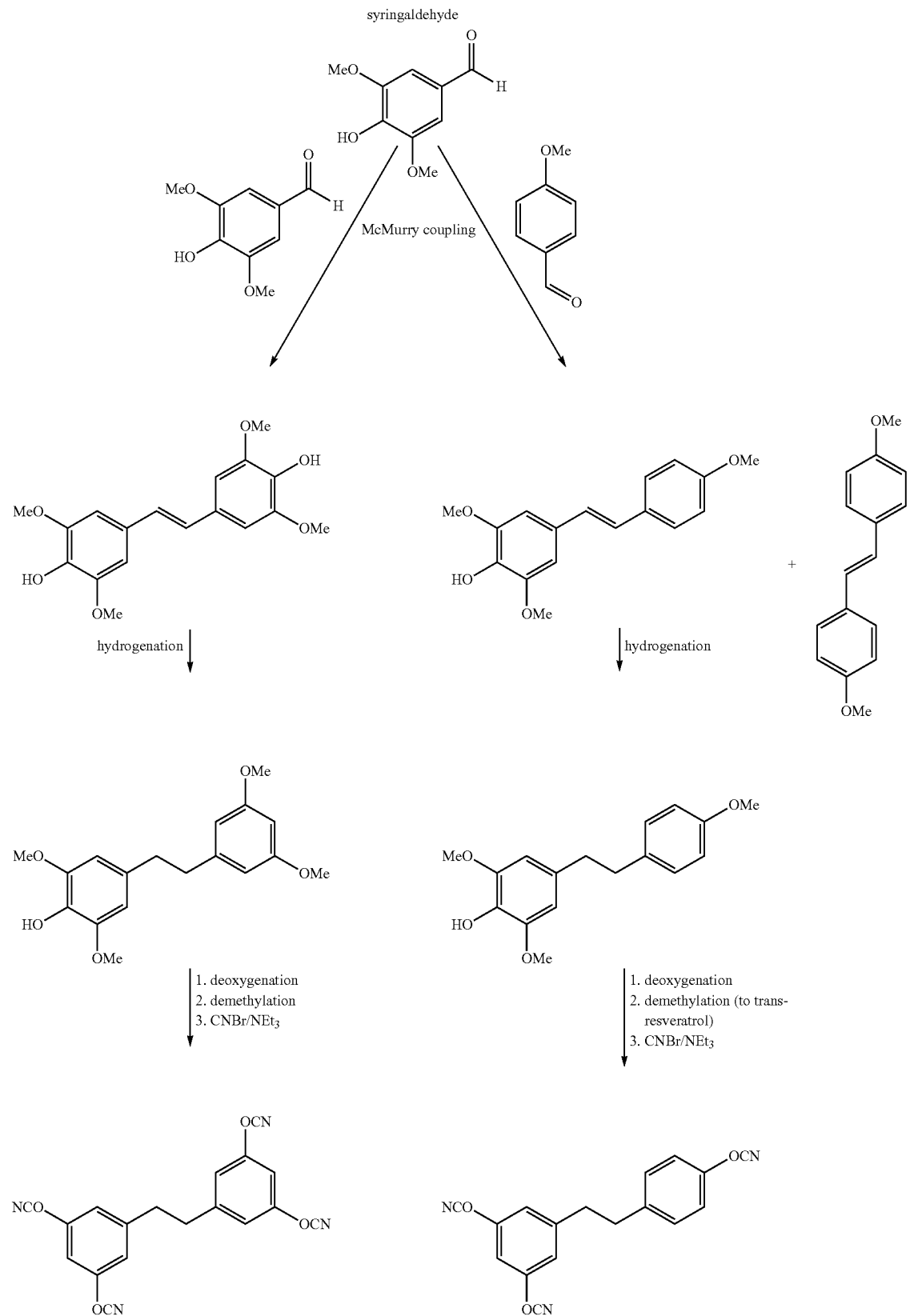

Scheme 3. Conversion of syringaldehyde to cyanate esters without initial dehydrodeoxygenation (electrochemical coupling)

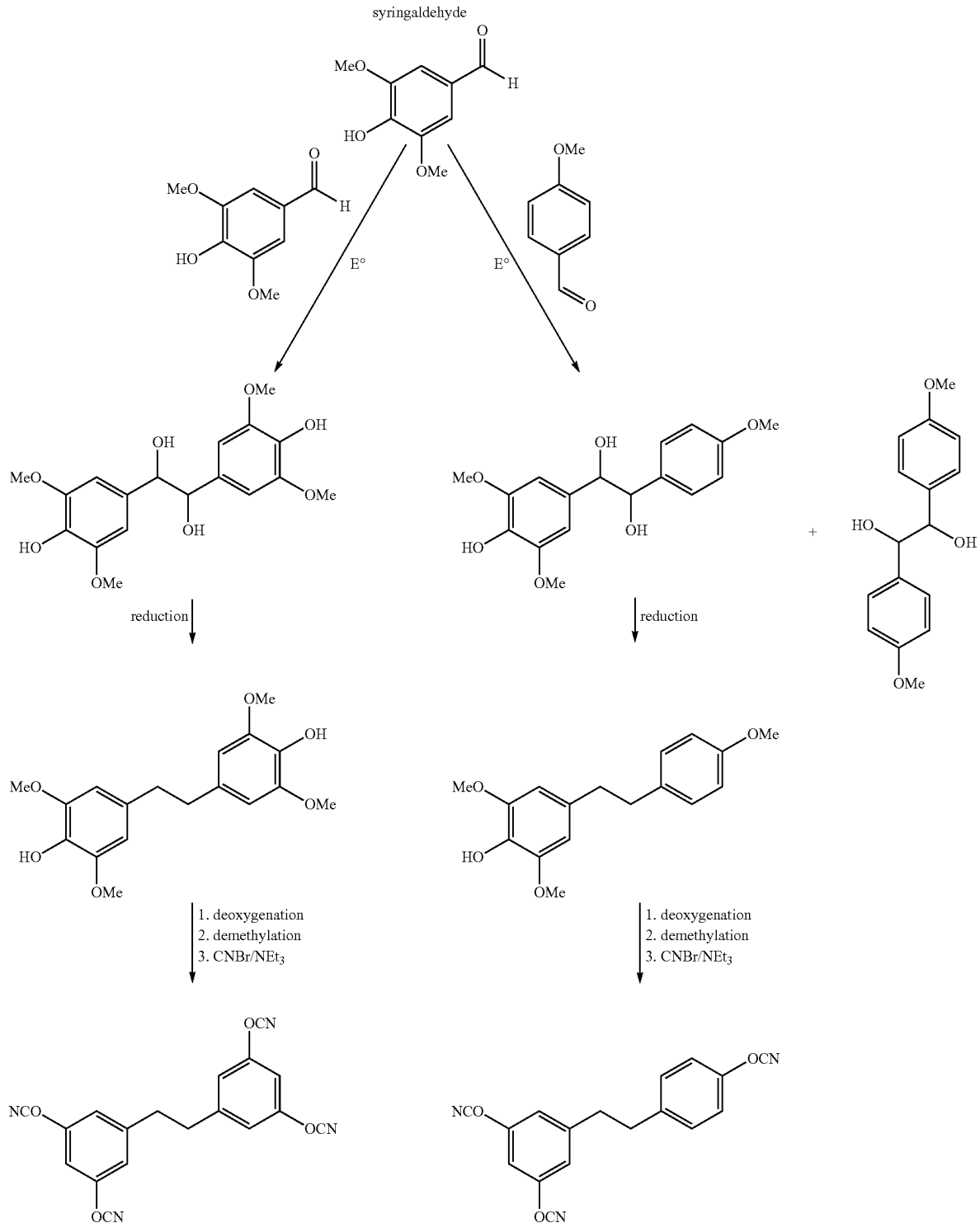

Embodiments of the invention generally relate to methods for making resins from syringaldehyde including, deoxygenating syringaldehyde by conversion to a sulfonate and reaction with a reductive elimination catalyst to produce 3,5-dimethoxybenzaldehyde, reductively coupling the dimethoxybenzaldehyde with at least one dimethoxybenzaldehyde or at least one aromatic aldehyde having a hydroxy group and/or methoxy group in at least one position on the aldehyde by a McMurry reaction or by reductive chemical or electrochemical reactions to produce at least one reductive coupling product, further reducing the reductive product(s) by hydrogenation, chemical reduction or electrochemical reduction followed by demethylating with a hydrolyzing reagent to produce polyphenols, and converting the polyphenols with a soluble base and cyanogen halide(s) or pseudohalides to produce cyanate ester resin(s).

An aspect of the invention generally relates to methods for making resins from syringaldehydes including, reductively coupling syringaldehyde with an additional molecule of syringaldehyde or at least one aromatic aldehyde having a hydroxy group, and/or methoxy group in at least one position on the aldehyde by a McMurry reaction or by reductive chemical or electrochemical reaction to produce at least one first reductive coupling product, further reducing the first reductive coupling product by hydrogenation or chemical reduction or electrochemical reduction to produce a second reductive coupling product, deoxygenating and demethylating the second reductive product(s) by conversion to a sulfonate followed by reaction with a reductive elimination catalyst and further reaction with a hydrolyzing reagent to produce polyphenols, and converting the polyphenols by reaction with a soluble base and cyanogen halide(s) or pseudohalides to produce cyanate ester resin(s). Other aspects of the invention further include thermoplastics, resins, and composites produced by the methods herein.

Embodiments further include converting the polyphenols by reaction with reagents including phosgene, triphosgene, diphenylcarbonate, other carbonates, bis(4-chlorophenyl) sulfone, other functionalized sulfones, diacid chlorides, phthalic acids, formaldehyde, other aldehydes, and epichlorohydrin to produce thermoplastics or resins selected from the group consisting of polysulfones, polyesters, polyesterstyrene polymers, alkylphenolics, polyarylates, polycarbonates, epoxy resins, and any combination thereof. In embodiments, the polyphenols are converted to thermosetting resins selected from the group consisting of cyanate ester resins, epoxy resins, benzoxazine resins, phenolic resins, bismaleimide resins, and polyether ether ketone (PEEK) resins. In embodiments, the resins are combined with the thermoplastics and fibers are thermally cured either with or without a catalyst to fabricate composite materials. In embodiments, the sulfonates are selected from the group consisting of mesylates, tosylates and triflates. In embodiments, the reductive elimination catalyst is selected from the group including zero valent nickel or palladium catalysts. In embodiments, the McMurry reaction includes catalysts selected from the group consisting of reducible titanium(III) or titanium(IV) compounds and reducing agents selected from the group consisting of lithium, sodium, potassium, zinc dust, zinc copper couple, magnesium, magnesium-mercury amalgam, and lithium aluminum hydride. In embodiments, the reductive coupling product produced by the McMurry reaction includes stilbenes. In embodiments, the stilbene is trans-resveratrol or cis or trans-3,3'-5,5'-stilbenetetrol.

In embodiments, the electrochemical coupling was accomplished using electrodes selected from the group consisting of lead, platinum, mercury, nickel, gold, and carbon and performed at a voltage at which hydrogen evolution occurs at the chosen electrode. In embodiments, the reductive coupling product produced by the reductive chemical or reductive electrochemical reaction results in a linking group between aromatic rings that selected from the group consisting of vicinal diols, alkenes, ketones, alcohols, and alkanes. In embodiments, hydrogenation is achieved by using a catalyst that include a transition metal selected from the group consisting of platinum, palladium, nickel, ruthenium, molybdenum, copper, and chromium and is conducted under a gas including hydrogen atmosphere.

In embodiments, the chemical reduction is achieved by protection of the vicinal diol to the diacetate or oxolate followed by reduction to a stilbene using the base with or without a reducing metal including zinc or magnesium. In embodiments, the electrochemical reduction is achieved by initial conversion of the vicinal diol to an oxalate or acetate followed by electrochemical reduction. In embodiments, the hydrolyzing reagent is selected from the group consisting of pyridinium hydrochloride, boron tribromide and other suitable reagents. In embodiments, the base is selected from the group consisting of alkyl amines including triethylamine, alkali and alkaline earth alkoxides, and other suitable bases. In embodiments, the cyanogen halide is selected from the group consisting of cyanogen bromide, cyanogen chloride, cyanogen iodide, and any combination thereof. In embodiments, the cyanogen pseudohalide is a cyanogen sulfonate, wherein the sulfonates are defined as $RSO_3^-$ (R=at least one alkyl or aromatic group).

Prophetic Examples

Any prophetic examples described herein are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making resins from syringaldehydes, comprising:
    reductively coupling syringaldehyde with an additional molecule of syringaldehyde or at least one aromatic aldehyde having a hydroxy group, and/or methoxy group in at least one position on said aldehyde by a McMurry reaction or by reductive chemical or electrochemical reaction to produce at least one first reductive coupling product;
    further reducing said first reductive coupling product by hydrogenation or chemical reduction or electrochemical reduction to produce a second reductive coupling product;
    deoxygenating and demethylating said second reductive product(s) by conversion to a sulfonate followed by reaction with a reductive elimination catalyst and further reaction with a hydrolyzing reagent to produce polyphenols; and converting said polyphenols by reaction with a soluble base and cyanogen halide(s) or pseudohalides to produce cyanate ester resin(s).

2. The method according to claim 1, wherein said resins are combined with said thermoplastics and fibers and are thermally cured with or without a catalyst to fabricate composite materials.

3. The method according to claim 1, wherein said McMurry reaction includes catalysts selected from the group consisting of reducible titanium(III) or titanium(IV) compounds and reducing agents selected from the group consisting of potassium, zinc dust, zinc copper couple, magnesium, magnesium-mercury amalgam, and lithium aluminum hydride.

4. The method according to claim 1, wherein said reductive coupling product produced by said McMurry reaction include stilbenes.

5. The method according to claim 4, wherein said stilbene is trans-resveratrol or cis or trans-3,3'-5,5'-stilbenetetrol.

6. The method according to claim 1, wherein said electrochemical coupling was accomplished by using electrodes selected from the group consisting of lead, platinum, mercury, nickel, gold, and carbon and performed at a voltage at which hydrogen evolution occurs at the chosen electrode.

7. The method according to claim 1, wherein said reductive coupling product produced by said reductive chemical or reductive electrochemical reaction results in a linking group between aromatic rings that is selected from the group consisting of vicinal diol(s), alkene(s), ketone(s), alcohol(s), alkane(s), and any combination thereof.

8. The method according to claim 1, wherein said hydrogenation is achieved by using a catalyst that includes a transition metal selected from the group consisting of platinum, palladium, nickel, ruthenium, molybdenum, copper, and chromium under a hydrogen atmosphere.

9. The method according to claim 1, wherein said chemical reduction is achieved by protection of said vicinal diol to the diacetate or oxalate followed by reduction to a stilbene using said base with or without a reducing metal including zinc or magnesium.

10. The method according to claim 6, wherein said electrochemical reduction is achieved by initial conversion of said vicinal diol to an oxalate or acetate followed by electrochemical reduction.

11. The method according to claim 1, wherein said sulfonates are selected from the group consisting of mesylates, tosylates and triflates.

12. The method according to claim 1, wherein said reductive elimination catalyst is selected from the group including zero valent nickel or palladium catalysts.

13. The method according to claim 1, wherein said hydrolyzing reagent is selected from a group consisting of pyridinium hydrochloride, boron tribromide and other suitable reagents.

14. The method according to claim 1, wherein said base is selected from the group consisting of alkyl amines including triethylamine, alkali and alkaline earth alkoxides, and other suitable bases.

15. The method according to claim 1, wherein said cyanogen halide is selected from the group consisting of cyanogen bromide, cyanogen chloride, and cyanogen iodide.

16. The method according to claim 1, wherein said cyanogen pseudohalide is a cyanogen sulfonate, wherein said sulfonates having $RSO_3^-$ (R=at least one alkyl or aromatic group).

17. Resins produced by the methods in claim 1.

18. Composites produced by the methods in claim 2.

* * * * *